United States Patent [19]
Petersen et al.

[11] Patent Number: 5,156,846
[45] Date of Patent: Oct. 20, 1992

[54] PERCUTANEOUS DRUG DELIVERY SYSTEM

[75] Inventors: Robert V. Petersen, Murray, Utah; Tsung-Min Hsu, St. Louis, Mo.

[73] Assignee: University of Utah, Salt Lake City, Utah

[21] Appl. No.: 773,766

[22] Filed: Oct. 10, 1991

Related U.S. Application Data

[63] Continuation of Ser. No. 314,819, Feb. 23, 1989, abandoned.

[51] Int. Cl.⁵ ............................................. A61F 13/00
[52] U.S. Cl. ...................................... 424/443; 424/449
[58] Field of Search .................... 424/443, 94.2, 449

[56] References Cited

U.S. PATENT DOCUMENTS

| | | | |
|---|---|---|---|
| 2,917,433 | 4/1956 | Goldman | 424/94.65 |
| 3,493,652 | 2/1970 | Hartman | 424/94.6 |
| 4,361,551 | 11/1982 | Galbraith | 424/94.2 |
| 4,666,441 | 5/1987 | Andriola et al. | 424/448 |
| 4,820,720 | 4/1989 | Sanders et al. | 542/356 |
| 4,910,205 | 3/1990 | Kogan et al. | 424/449 |

*Primary Examiner*—Thurman K. Page
*Assistant Examiner*—Leon R. Horne
*Attorney, Agent, or Firm*—Trask, Britt & Rossa

[57] ABSTRACT

A percutaneous drug delivery system, method, and kit are disclosed. The method comprises applying an enzyme preparation to a localized area of skin for a predetermined amount of time to enhance that area of skin's permeability to selected drugs, occluding the area of skin during the application, and then applying the selected drug(s) to the area of skin to allow the drug to penetrate through the skin and into the circulatory system of the animal. Greatly enhanced penetration of chemicals through the skin results from the enzyme treatment.

12 Claims, 12 Drawing Sheets

URINARY RECOVERY OF ¹⁴C-TEAB

5,156,846

PERCUTANEOUS DRUG DELIVERY SYSTEM

This application is a continuation, of application Ser. No. 07/314,819, filed Feb. 23, 1989 now abandoned.

BACKGROUND OF THE INVENTION

1. Field

This invention pertains to drug delivery systems generally and is more particularly directed to transdermal drug delivery systems and methods.

2. State of the Art

Devices for transdermal or percutaneous drug delivery are known in the art. Such devices include "patches" such as the Nitro-Dur ® nitroglycerin transdermal infusion system marketed by Key Pharmaceuticals of Kenilsworth, N.J. This system consists of a "patch" containing nitroglycerin in acrylicbased polymer adhesives with a resinous cross-linking agent to provide a continuous source of nitroglycerin to the patient. The patches are available in various dosage strengths for delivering various amounts of nitroglycerin to the patient over a twenty-four hour period. These patches vary in size from five to thirty square centimeters ($cm^2$). The rated release of the drug is dependent upon the area of the patch with 0.5 milligram (mg) being released for every square centimeter of patch per 24 hours. The patch is applied to any convenient skin area, especially the arm or chest.

Another transdermal patch is marketed by Noven Pharmaceutical of Miami, Fla. The Noven patch has been used with nitroglycerin and estrogen. It consists of a nonocclusive backing layer, a drug reservoir for containing the drug, a microporous rate controlling membrane which contacts the skin of the patient, and an adhesive formulation for keeping the patch in contact with the skin. Drug passes from the reservoir through the membrane, through the patient's skin, and into the bloodstream.

Another transdermal patch, Transderm SCOP ®, is used by CIBA Consumer Pharmaceutical Co. of Summit, N.J. It is a film 0.2 mm thick and 2.5 $cm^2$, with four layers. Proceeding from the visible surface towards the surface attached to the patient's skin (FIG. 12), these layers are: (a) a backing layer of tan-colored, aluminized, polyester film; (b) a drug reservoir of scopolamine, mineral oil, and polyisobutylene; (c) a microporous polypropylene membrane that controls the rate of delivery of scopolamine from the system to the skin surface; and (d) an adhesive formulation of mineral oil (12.4 mg), polyisobutylene (11.4 mg) and scopolamine (1.5 mg). A protective peel strip of siliconized polyester, which covers the adhesive layer, is removed before the system is used. The inactive components, mineral oil and polyisobutylene, are not released from the system. The system is "programmed" to deliver 0.5 mg of scopolamine at an approximately constant rate of the systemic circulation over the three-day lifetime of the system. An initial priming dose of scopolamine, released from the adhesive layer of the system is believed to saturate the skin binding sites for scopolamine and bring the plasma concentration of scopolamine to the required steady state level. A continuous controlled release of scopolamine, which flows from the drug reservoir through the rate-controlling membrane, maintains the plasma level constant.

A similar system is also used by CIBA Pharmaceutical Company in its Transderm-Nitro ® nitroglycerin. In this system, the rate controlling membrane is an ethylene/vinyl acetate copolymer membrane that is permeable to nitroglycerin, and the adhesive used is a hypoallergenic silicone adhesive.

Another system to deliver drugs through the skin of a patient is disclosed in French patent 2,556,218. This patent discloses "sticks" for roll-on application of a desired drug. These sticks contain, as components, an enzymatic penetrating agent, the desired drug, and various excipients. The enzymatic penetrating agents disclosed include alpha-chymotrypsin and hyaluronidase. Drugs disclosed for use with these sticks include aspirin, lidocaine, lutadine, vitamin A, and tetracycline. Excipients disclosed include sodium glycerol stearate. The desired drug, enzymatic penetrating agent, and excipient can be mixed together to form a homogeneous mixture.

Alternatively, the various components of the stick can be separated from one another in a manner that brings one component (e.g., enzymatic penetrating agent) immediately after the other (e.g., drug) in contact with the local application zone of the patient's skin for treatment (e.g. a solid stick can make up two longitudinal or concentric parts of one stick). The enzymatic penetrating agents increase the penetration of the desired drug through the patient's skin or mucous membrane.

Another transdermal drug delivery system is disclosed in French Patent No. 2,448,903. This system consists of at least one antibiotic, an enzyme, an antiinflammatory agent, and/or a local anesthetic agent, and/or a heteratolytic agent, and/or a mucolytic agent, and/or an emulsifying agent. Enzymes disclosed include hyaluronidase, streptokinase, streptodonase, trypsin, chymotrypsin, $\alpha$-chymotrypsin; $\alpha$-amylase, bromelain, papain, desoxyribonuclease, collagenase, and sutilain. This system is used to provide localized antibiotic therapy.

None of these prior art systems have fully utilized proteolytic enzymes' ability to increase an animal's skin's permeability to permit the transdermal delivery of a drug.

SUMMARY OF THE INVENTION

The invention includes a method of delivering a drug to an animal having skin comprising: 1) applying and keeping in contact a proteolytic enzyme preparation to a localized area of the animal's skin in a sufficient quantity to enhance that area of skin's permeability to a selected drug over a predetermined amount of time; 2) occluding the area of skin with occlusion means for an amount of time sufficient to allow the enzymatic preparation to enhance the skin's permeability to the selected drug; 3) removing the occlusion means and rinsing the area of skin; and 4) applying the selected drug, in solution, to the area of skin. As used herein, "animal" includes human beings. Optionally, the skin may be 5) again occluded after the application of the selected drug.

The invention further includes a drug delivery system. This drug delivery system includes an enzyme preparation, means for applying the enzyme preparation to an area of skin, a membrane for occluding the area of skin after the enzyme preparation has been applied; a drug; and means for applying the drug to the area of skin.

The drug delivery system can be a dual patch percutaneous drug delivery device which includes: a first patch sized and adapted to contact a localized area of skin. This first patch contains, in a reservoir, an effective amount of a proteolytic enzyme. The drug delivery device further includes a second patch attached to the first patch in a common structure. This second patch is also adapted to contact the localized area of skin after the first patch has been removed from the skin. This second patch contains an effective amount of a preselected drug, preferably in liquid form, for administration percutaneously.

The drug delivery system of the present invention can also be a dual-patch, percutaneous drug delivery kit. This kit includes: 1) a first patch containing enzyme or enzymes; 2) a second patch containing drug or drugs, and 3) structure adapted to receive the first and second patches serially, i.e. sequentially, so that the second patch is removable from the structure only after the first patch is removed.

DETAILED DESCRIPTION OF THE PREFERRED EMBODIMENTS

Enzymes useful in the enzyme preparations of the present invention are enzymes capable of altering structures of the skin of the particular animal to be treated so as to enhance the skin's permeability to a selected drug or drugs. Enzymes preferred for these purposes do not substantially react detrimentally with the selected drug, do not degrade substantially to an inactive state at body temperature or in solution; do not cause unacceptable discoloration or scarring of the skin, and react in sufficiently small concentrations to be useful over a relatively small area of skin. A preferred enzyme is papain, which is readily available from Allergan of Irvine, Calif., Sigma Chemical Company of St. Louis, Mo., and other sources.

Other enzymes useful in the practice of the invention include pancreatin (actually a mixture of enzymes), ficin, bromelain, elastase, and pepsin.

Other enzymes which may be useful include hyaluronidase, streptokinase, streptodonase, trypsin, chymotrypsin, α-chymotrypsin, α-amylase, desoxyribonuclease, collagenase, sutilain, and other specific and non-specific proteolytic enzymes. For purposes of this disclosure, a non-specific proteolytic enzyme is one that alters a protein's structure at nearly any point or level, including breaking down disulfide bonds, which can result in complete denaturation of the skin protein. A specific proteolytic enzyme, however, is one that merely alters the protein under conditions not sufficiently severe to alter protomer configuration. Specific proteolytic enzymes, such as papain and pancreatin, are accordingly therefore preferred in the practice of this invention; although the nonspecific proteolytic enzymes, such as bromelain and ficin, will also work.

Whatever the enzyme or enzymes selected, each is typically admixed with a liquid, such as water or ethanol to form an enzyme preparation. The concentration of enzymes(s) in liquid will be of a sufficient quantity to increase the skin's permeability to selected drugs over a predetermined time period. Preferably, the concentration of enzyme(s) in the enzyme preparation will be great enough to alter the skin's permeability to the selected drug in less than 24 hours for practical reasons. Concentrations of papain in water will generally be greater than about 0.019 milligrams/milliliter (mg/ml). Preferred concentrations of papain in water will be less than about 0.093 mg/ml. Pretreatment of skin samples with papain concentrations greater than 0.093 mg/ml at pH 7.4 leads to greater drug penetration, but also damages the skin, possibly leading to bleeding.

Figure 19:
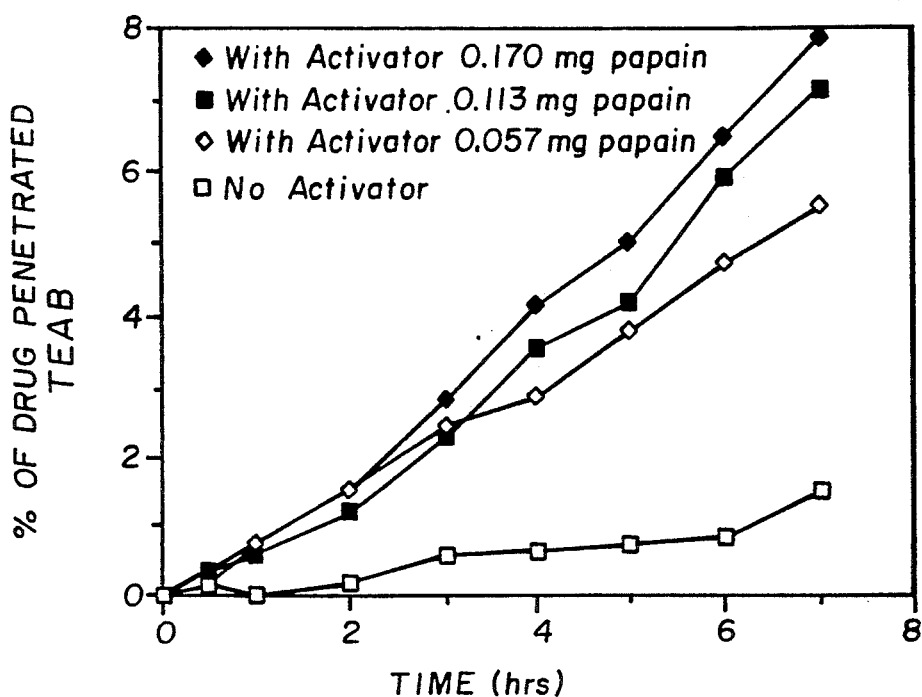
FIG. 19 depicts the enhancement of TEAB penetration through mouse skin by the use of an enzyme preparation containing papain at varying levels and with and without an activating agent per Example 7C.

Some enzyme preparations will also include "activating agents" (see Example 7C and FIG. 19). These activating agents enhance the percutaneous delivery of the drug(s) through the skin. For example, papain from Sigma Chemical may be activated with the chelating agent ethylenediaminetetraacetic acid ("EDTA"). EDTA activation of papain increases the penetration of tetraethylammonium bromide through the skin in comparison to use of the papain without such activation. Papain from Allergan, on the other hand, requires no such activation. Amounts of EDTA in a papain enzyme preparation will vary from 2 mg/ml to about 20 mg/ml. The amino acid cysteine can also serve as an activating agent.

An especially preferred activating agent for use with papain is 0.10 molar cysteine in combination with 0.0375 molar EDTA which activated the papain to achieve greater penetration of drug through the skin.

Ideally, the enzyme preparations are compounded to retain stability for long periods of time. Various factors, such as composition, pH and ionic strength of the solution, and the chosen solvent, influence the stability of the enzyme preparations. For maximum stability, when enzymes such as papain and bromelain are used, the enzyme preparation should be dissolved in water, and have a pH of from about 3 to about 10.

The enzyme or drug preparation may also be stabilized with various preservatives. Considerations in selecting an agent for use as a preservative in the system, as with most pharmaceutical preparations, include: a) the agent's spectrum of activity; b) the agent's stability over allergenic potential; e) the agent's compatibility with the other constituents of the preparation, and f) the agent's odor. Various alcohols, e.g. ethanol or isopropanol; quaternary ammonium surfactants; and other compounds well known to those skilled in the art may be used as a preservative. The United States Pharmacopeia XXI 1985, contains a section on stability considerations in compounding at pages 1345 through 1347, the contents of which are incorporated by this reference.

For maximum sustained penetration of drug(s) through treated skin, the pH of the enzyme preparation will vary from 5.8 to 8.0, with the preferred pH being about 7.4.

The enzyme preparation can be applied using any of several well-known techniques for applying a liquid to a surface. For example, a brush, swab, or spray container containing the preparation may be used to apply the preparation to the skin.

Figure 1:
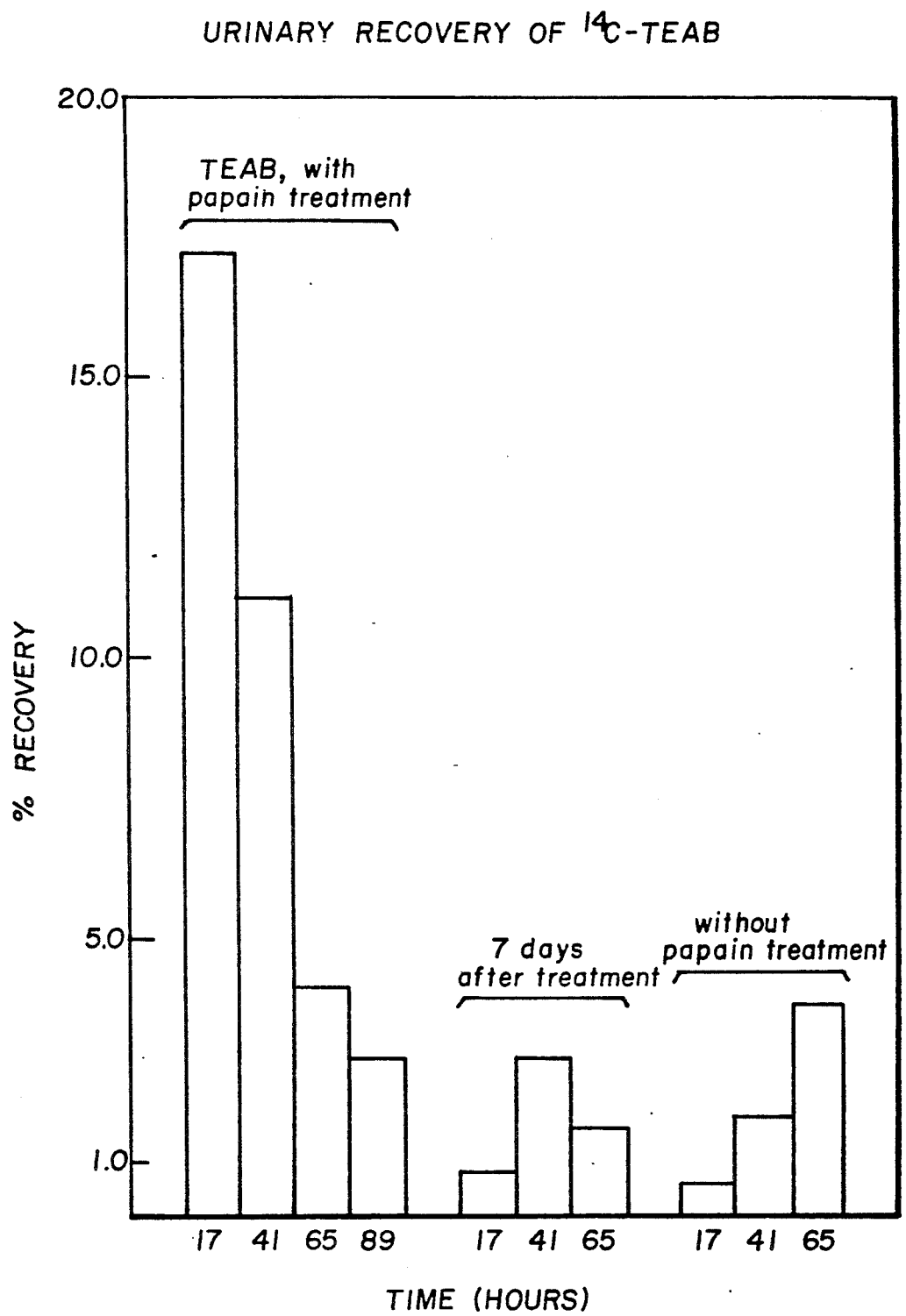
FIG. 1 is a graph comparing the percentage urinary recovery of $^{14}C$-TEAB with papain treatment, seven days after papain treatment, and without papain pretreatment per Example 1.
Figure 2:
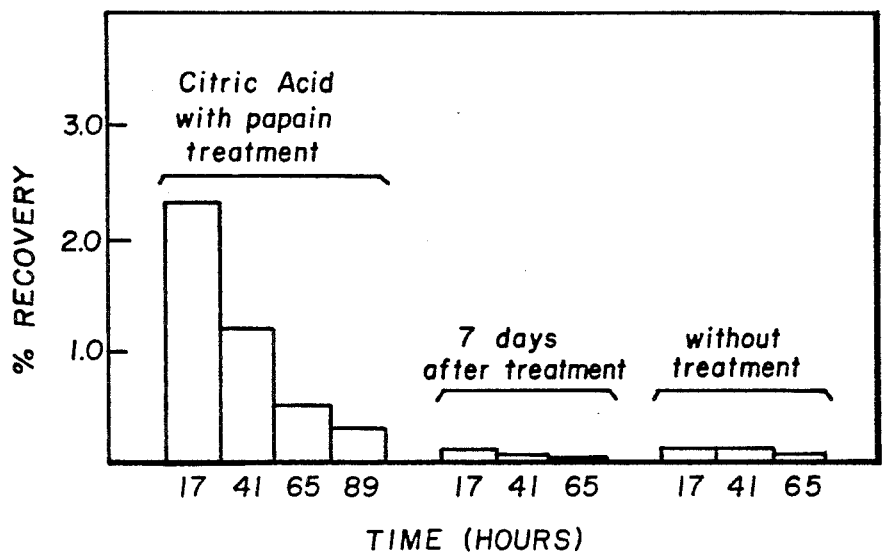
FIG. 2 is a graph comparing the percentage urinary recovery of $^{14}C$-Citric acid with papain treatment, seven days after papain treatment, and without papain pretreatment per Example 1.
Figure 3:
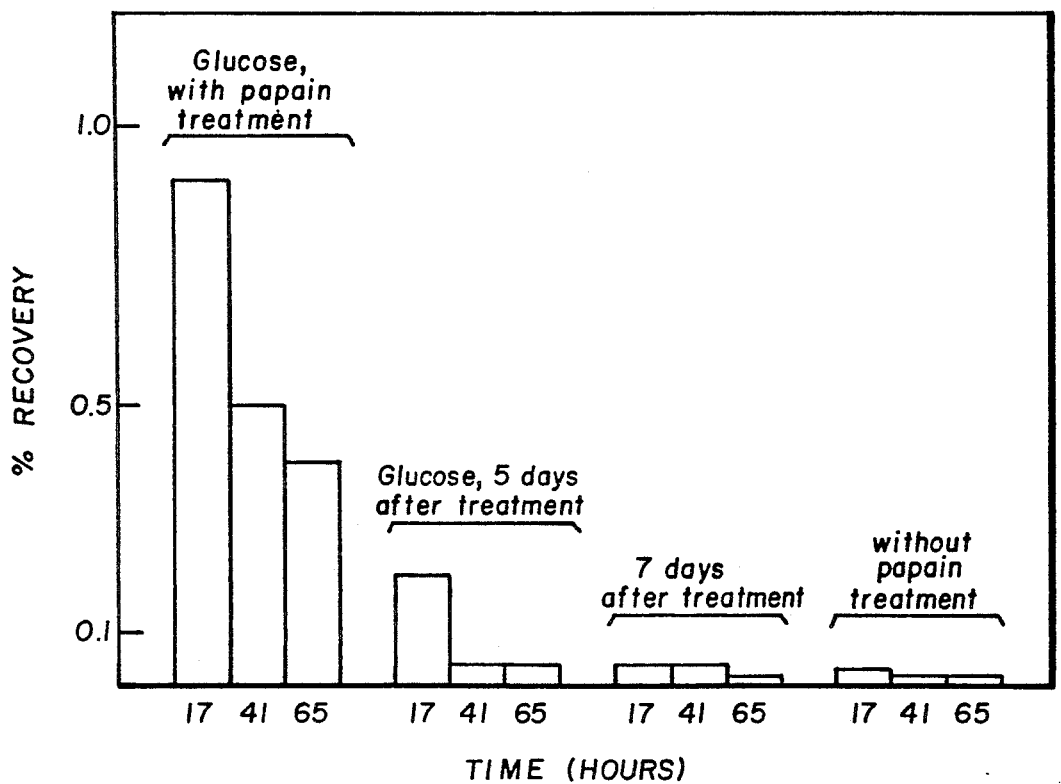
FIG. 3 is a graph comparing the percentage urinary recovery of $^{14}C$-glucose with papain treatment; five days after papain treatment; seven days after papain treatment; and without papain pretreatment per Example 1.
Figure 4:
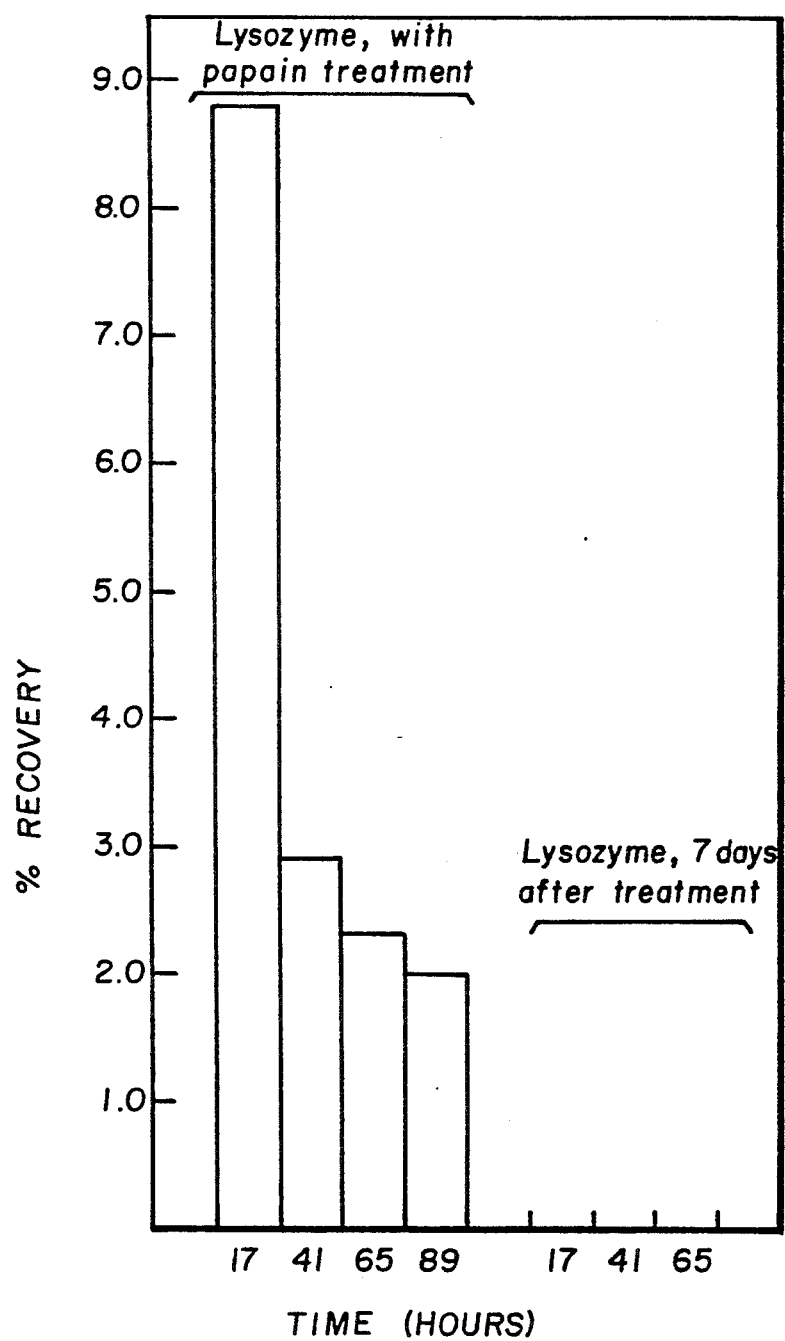
FIG. 4 is a graph comparing the percentage urinary recovery of the $^{14}C$-protein lysozyme with papain treatment, and seven days after treatment, as per Example 1.
Figure 5:
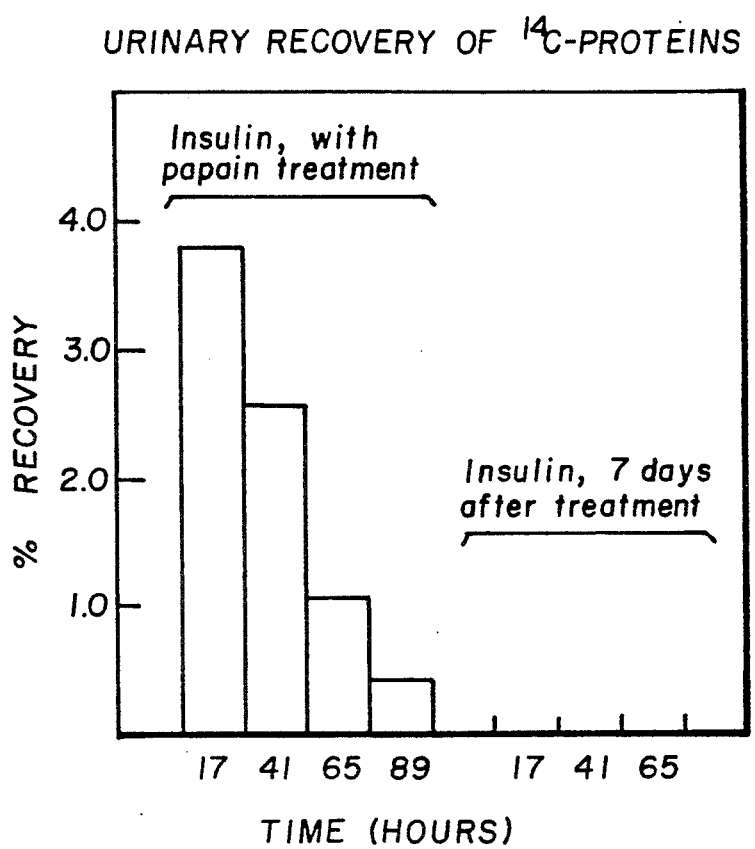
FIG. 5 is a graph comparing the percentage urinary recovery of the $^{14}C$-protein insulin with papain treatment and seven days after treatment per Example 1.
Figure 6:
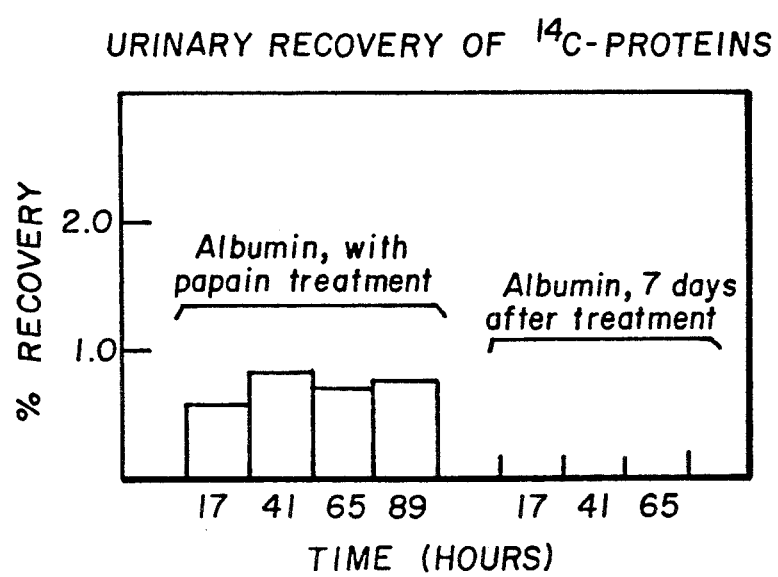
FIG. 6 is a graph comparing the percentage urinary recovery of $^{14}C$-protein albumin with papain treatment and seven days after treatment per Example 1.
Figure 7:
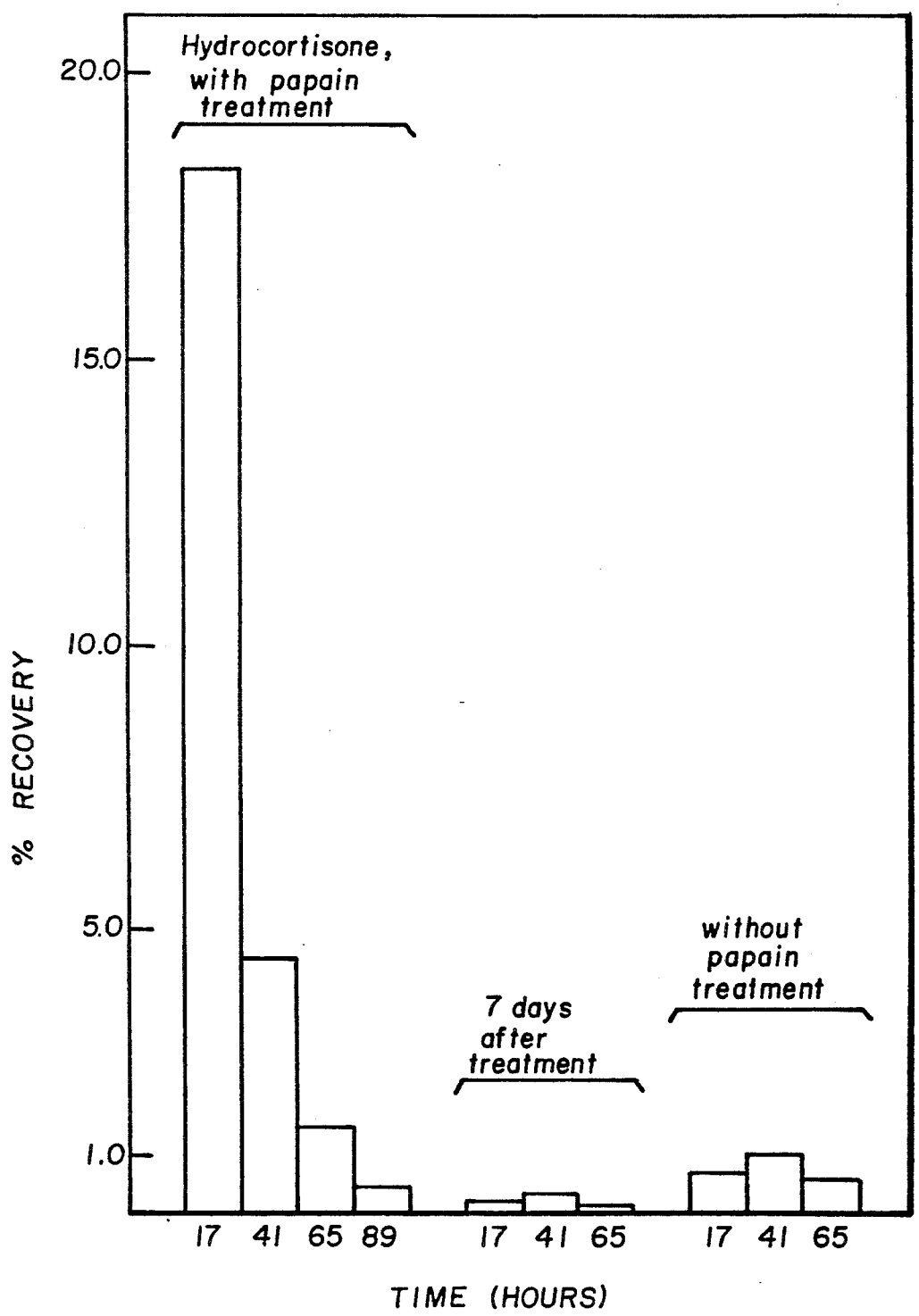
FIG. 7 is a graph comparing the percentage urinary recovery of $H^3$-Hydrocortisone with papain treatment, seven days after papain treatment, and without papain treatment as per Example 1.
Figure 8:
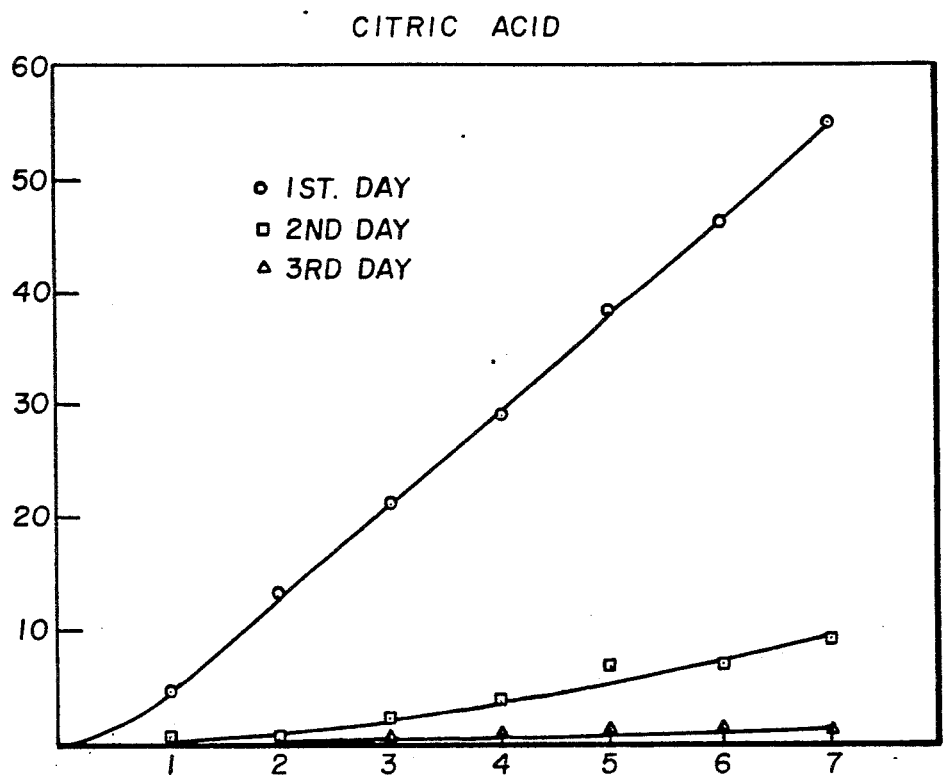
FIG. 8 shows the saturation coefficient of citric acid, and the flux, permeability coefficient, and graph for citric acid first day (immediately following 24-hour exposure to papain), second day (24 hours following 24-hour exposure to papain) and third day (48 hours following 24-hour exposure to papain) as per Example 2.
Figure 9:
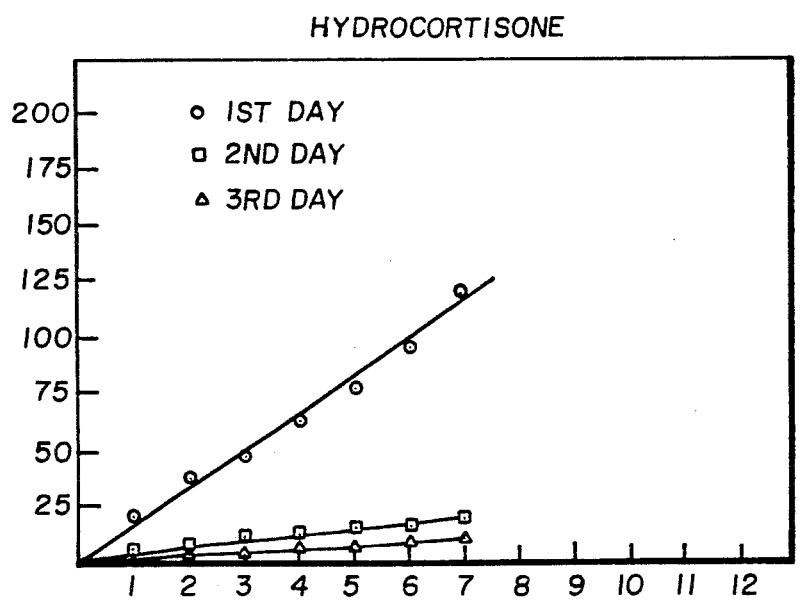
FIG. 9 shows the saturation coefficient of hydrocortisone, and the flux, permeability coefficient and graph for hydrocortisone first day (immediately following 24-hour exposure to papain), second day (24 hours following 24-hour exposure to papain), and third day (48 hours following 24-hour exposure to papain) as per Example 2.
Figure 10:
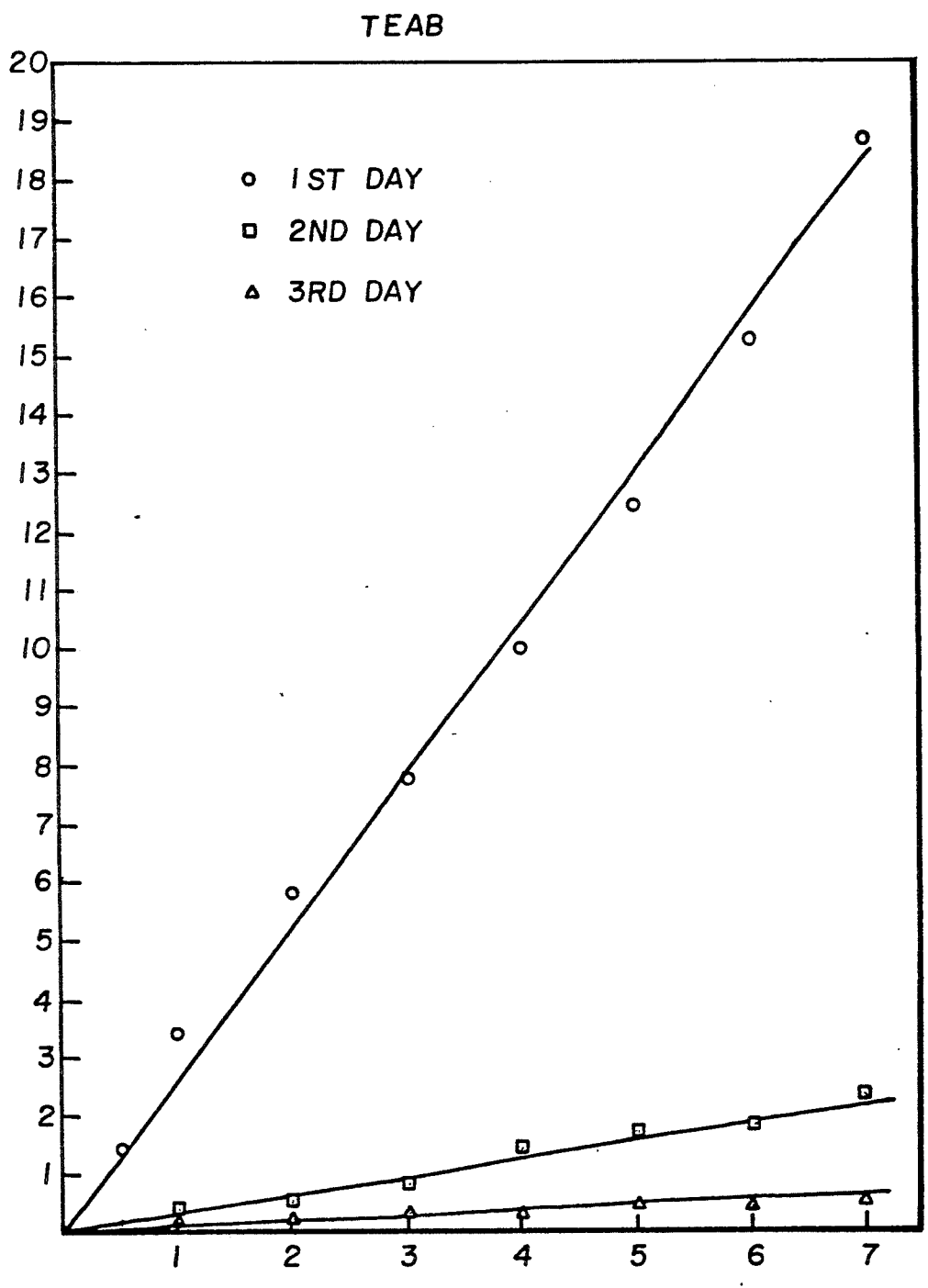
FIG. 10 shows the saturation coefficient of TEAB and the flux, permeability coefficient, and graph for TEAB first day (immediately following 24-hour exposure to papain), second day (24 hours following 24-hour exposure to papain), and third day (48 hours following 24-hour exposure to papain) as per Example 2.
Figure 11:
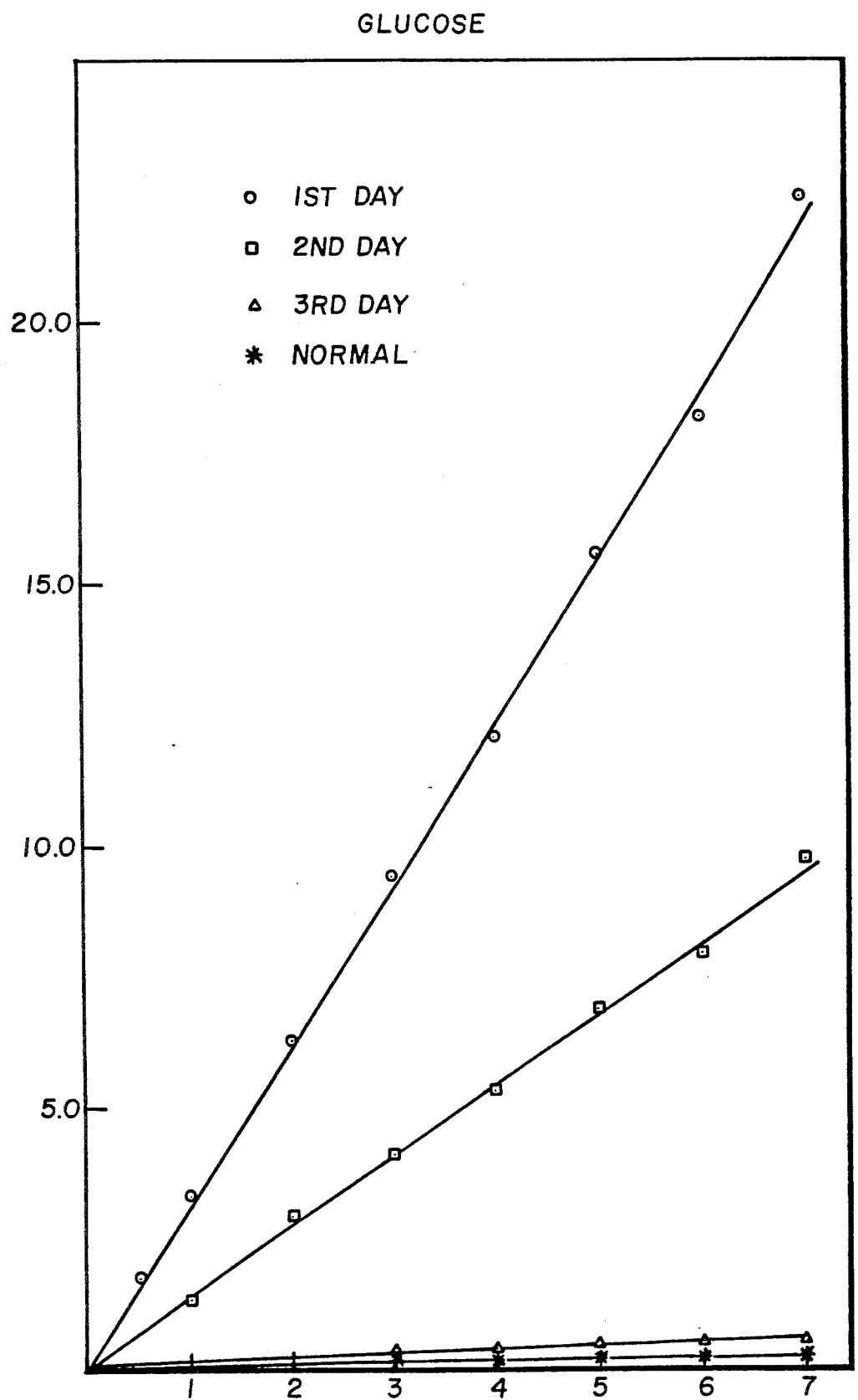
FIG. 11 shows the saturation coefficient of glucose, and the flux, permeability coefficient, and graph for glucose first day (immediately following 24-hour exposure to papain), second day (24 hours following 24-hour exposure to papain), and third day (48 hours following 24-hour exposure to papain) as per Example 2.
Figure 12:
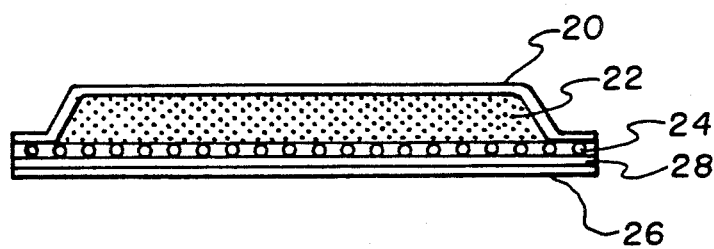
FIG. 12 stylistically depicts a side view of a prior art patch useful in the practice of the invention.

In a particularly preferred embodiment, the enzyme preparation is contained within a reservoir of a "patch" which is placed on the animal's skin. As shown in FIG. 12, which is a side view of a typical patch, the patch would include a backing 20, a reservoir 22 to contain the enzyme preparation, a membrane 24 to contain and release the contents of the reservoir, and a protective peel strip 26 or strips. Patches are typically round or oblong when viewed from above, and are preferably sized to affix neatly to the animal's skin. The membrane 24 is typically ratecontrolling or semi-permeable to the contents of the reservoir 22. Around the outer circumference of a patch, adhesive 28 is placed between the membrane 24 and a separate protective peel strip 26 so that the patch will adhere to the animal's skin.

Adhesives are preferably hypoallergenic substances which are useful in retaining the protective peel strips to the patch and the patch to the animal's skin. Preferred adhesives include silicone adhesive formulations and other adhesives well known to those skilled in the art.

One reason a patch is particularly preferred is that the occlusion means are included as part of the system, i.e., the backing 20. Other occlusion means include aluminized plastic, plastic film such as Saran Wrap ™, and Bioclusive tape ™. The important factors to consider when selecting occlusion means are a) that it not react with the contents of the reservoir, b) that it generally contain the contents to the desired localized area of skin, and c) that it not react detrimentally with the skin. In the case of use with humans, the backing is preferably skin-colored for cosmetic reasons.

When a patch is used as part of the system, the protective peel strip is removed from the patch, and the patch applied to the skin. The enzyme preparation permeates through the membrane, and contacts the skin. While a precise mechanism, or mechanisms, has not been empirically determined, the following theory may help to explain how the system works. Upon contact with the skin, the enzyme preparation seems to alter temporarily the skin's structure to increase the skin's permeability to various drugs, thus allowing the drugs to penetrate the skin more readily. One theory is that the enzyme preparations temporarily disrupt sulfhydryl bonds, thereby altering the skin's structure to allow penetration of the selected drug(s). Once the enzyme preparation has been removed from the skin, however, the skin's impermeability to these drugs preferably returns, after time (e.g., 48 hours), to its "normal" pretreatment state.

After the skin's structure has been sufficiently altered to allow enhanced passage of the selected drug through the skin, the enzyme-containing patch is removed.

The selected drug or drug preparation, also preferably in a liquid form, is then applied to the skin. The drug or drug preparation can be applied in the same ways previously described for the enzyme preparation. For example, a drug may be contained within the reservoir 22 of a patch to be applied to the same localized area of skin as previously treated with the enzyme preparation. Such a reservoir would preferably contain the drug in a sufficient concentration to allow therapeutic levels of the drug to pass through the skin to the animal's circulatory system.

Selected drugs are preferably ionic compounds such as anionic, cationic and zwitterionic chemicals, although the system can be used with various nonionic and nonpolar chemicals as well.

Selection of the drug will be dependent upon the disease state and animal to be treated. Ideal drugs for percutaneous drug delivery in accordance with the invention include hormones such as progesterone; quaternary compounds such as acetylcholine; and anionic chemicals such as coumadin. Therapeutic classes of drugs for use in the system include anti-hypertensive agents such as betablockers; anti-nauseants such as chlorpromazine; and antiarrythmics; and analgesics.

For active ingredients, i.e., enzymes or drugs, which are not stable in solution for sufficiently long periods of time, the enzyme, enzymes, drug or drugs can be mixed with solvent and then injected with a syringe or otherwise introduced into the reservoir of the patch immediately prior to the patch's application to the animal's skin.

The invention allows for the controlled and timed release of drugs to the animal. By increasing the concentration of drug in the drug-containing patch, the amount of drug which passes through the skin can be increased and the duration of drug application increased.

Figure 15:
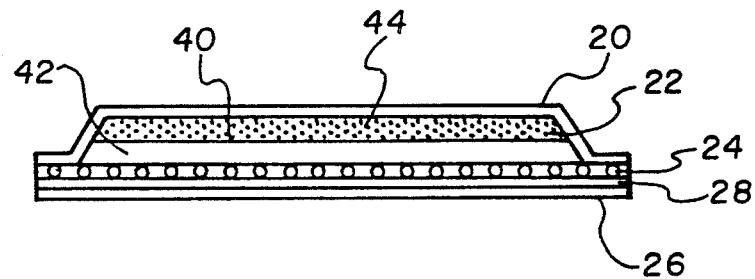
FIG. 15 depicts the side view of a patch useful in the practice of the invention.
Figure 16:
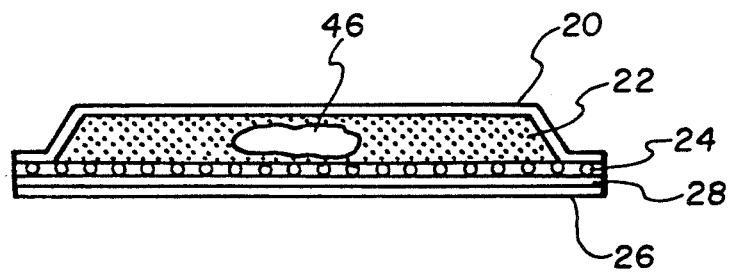
FIG. 16 depicts the side view of a patch useful in the practice of the invention.

Alternatively, as depicted in FIG. 15, an impermeable membrane 40 can be constructed into the reservoir 22 of the patch to divide the reservoir into two distinct compartments 42, 44. One compartment 42 contains the active ingredient in a dry, stable form, while the other compartment 44 contains the solvent with which the active ingredient is to be admixed. Alternatively (FIG. 16), the dry active ingredient or solvent could be contained within a breakable impermeable container 46 such as a capsule, within the reservoir 22, separating it from the other component. The impermeable membrane or capsule wall could then be purposely ruptured, and the dry active ingredient and solvent mixed to form the particular preparation within the reservoir. The patch is applied to the selected localized area of skin for administration of the particular active ingredient.

The localized area of the skin to which the enzyme and drug preparations are applied is preferably a relatively thin layer of skin, and other areas, such as the sole of the foot, should be avoided. Furthermore, hairy areas of skin should be avoided, or the hair first removed.

Figure 13:
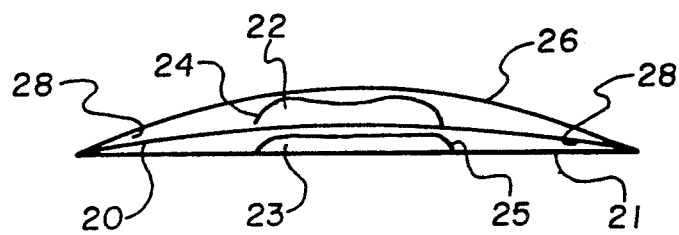
FIG. 13 stylistically depicts the side view of a dual patch drug delivery device according to the invention.

FIG. 13 depicts an alternate patch for use with the invention. It, like the patch depicted in FIG. 12, has a protective peel strip 26 which is removed to expose a membrane 24 and backing 20 containing an enzyme preparation contained within reservoir 22. Once the protective peel strip 26 has been removed, the patch depicted in FIG. 13 may be applied to the localized area of skin of the animal to be treated for the amount of time needed to increase the skin's permeability to the drug preparation contained within the other reservoir 23. Backing 20, which in this embodiment also serves as a protective peel strip for the reservoir 23 containing the drug preparation, is separated from the second backing 21 of the patch, thus exposing the membrane 25 which along with the second backing 21 contains the reservoir 23 for the drug preparation. The membrane 25 and backing are then placed onto the patient's skin in the same location as where the enzyme preparation containing reservoir 22 was placed on the skin. Adhesive 28 serves both to keep the entire patch together, and to keep the respective portions of the patch attached to the patient's skin.

Drug contained within the drug preparation in reservoir 23 passes through the membrane 25 and onto the patient's enzyme-treated skin. The drug then passes through the skin and into the patient's circulatory system.

Heretofore, those skilled in the art have failed to realize the full potential of an enzyme preparation's capabilities to enhance the skin's permeability to drugs. Previously, the enzyme preparations and selected drugs were applied simultaneously, or nearly simultaneously and the full enhancement of permeability was not recognized. In contrast, the present system more effectively utilizes enzymes' enhancement capabilities to allow more precise administration of the drug, thus decreasing a) side effects, b) the amount of drug and enzyme needed, and c) the size of the system. Furthermore, problems of chemical incompatibilities between the drug(s) and the enzyme(s) are lessened so that a potentially greater number of drugs can be administered percutaneously.

In one embodiment of the system, the system is present in a kit form. Included in this kit are means for applying the enzyme preparations, occlusion means, and means for applying the selected drug. Means for applying the enzyme preparation and selected drug may be differently marked patches, each containing either the drug or the enzyme preparation. Different marking include different coloration of the patches and/or the protective peel strips. All components of the kit are contained within a convenient package for use by a medical or veterinary practitioner or patient.

The kit may also include means for mixing the enzyme with solvent such as a small glass container containing a solvent selected for the enzyme; means for mixing the selected drug(s) with solvent such as a small glass container containing a solvent selected for the drug; and means for introducing active ingredient preparations into the patches such as a needle-bearing syringe. These various means would typically be included with the kit when either, or both active ingredients or constituents thereof are not stable when premixed in solution for sufficient lengths of time to be useful in a kit.

Figure 14:
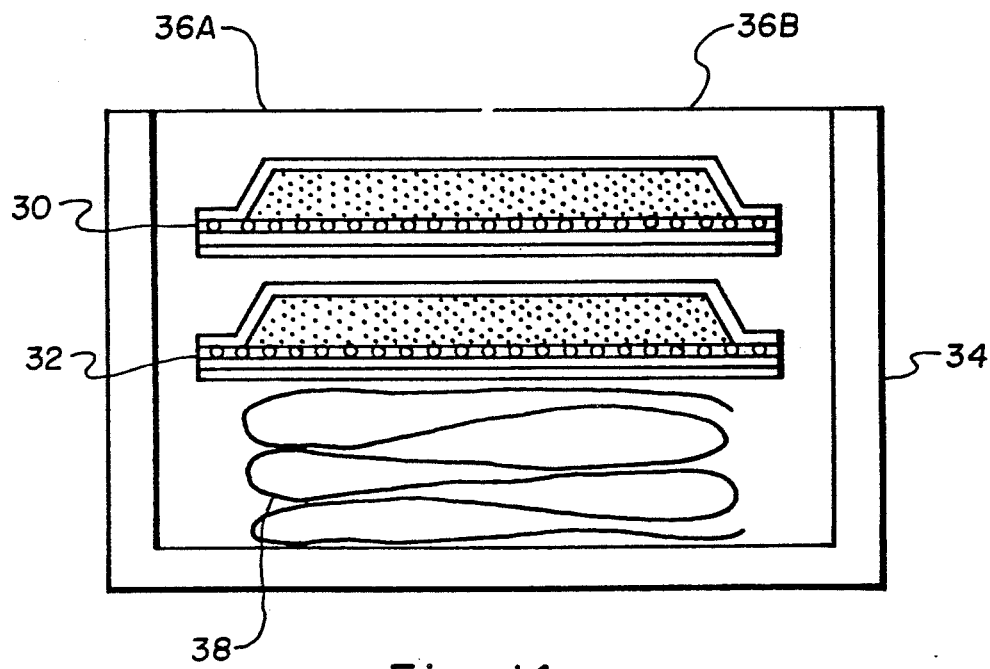
FIG. 14 stylistically depicts the side view of one embodiment of a dual patch percutaneous drug delivery kit according to the invention.

One embodiment of a percutaneous drug delivery kit is shown in FIG. 14. It includes a first patch 30 containing an enzyme preparation; and a second patch 32 containing a drug selected to be delivered percutaneously, contained within a container 34. Associated with the container are flaps 36A, 36B for retaining the patches 30, 32 within the container 34. The container may contain extension means such as spring 38 to press the patches 30, 32 against the flaps 36A, 36B.

A person using the kit removes the first patch 30 from the container 34 through the flaps 36A, 36B. The flaps 36A, 36B may be made of any material which is flexible, yet strong enough to retain the patches 30,32 within the container 34 against the force of the spring 38. The first patch is then applied to a localized area of the patient's skin for a predetermined time as previously described. After the predetermined time has passed, the person using the system removes the first patch 30 from the skin. The second patch 32 is then removed from the container 34 and the second patch 32 is then applied to the localized area of the skin for administration of the drug.

The following examples further assist in describing the invention.

EXAMPLE 1

1A. Enhancement of Model Drugs and Proteins Through Nude Mouse Skin by a Proteolytic Enzyme (Papain)

Various anionic, cationic, and nonionic chemicals were utilized as model compounds to determine the influence of proteolytic enzymes of the transdermal penetration of these substances. The model chemicals included: $^{14}$-C-labeled tetraethylammonium bromide (TEAB), a cationic substance; $^{14}$-C-labeled citric acid, an anionic substance; $^{14}$-C-labeled glucose, a highly polar nonionic substance; and $^{3}$-H-labeled (tritiated) hydrocortisone, a highly nonpolar, nonionic substance. Additional studies were performed using $^{14}$-C-labeled albumin, lysozyme, and insulin to determine the ability of the proteolytic enzymes to enhance the percutaneous absorption of larger molecules.

Enzyme preparations were prepared by dissolving one papain-containing tablet (Allergan, 144 mg) in 2 ml Phosphate Buffer Saline (PBS) solution. Two hundred µl of this solution was applied on to 1 cm$^2$ areas on the back of congenitally athymic nude mice. The 1 cm$^2$ areas were covered with folded gauze pads to absorb the excess papain solution, then the areas were occluded with a transparent dressing (Bioclusive Tape) and an adhesive tape. Each mouse was individually housed in separate cages for 24 hours. At the end of this time, residual papain on the surface of the mouse's skin was removed by washing. After cleansing the skin, 150 µl of radiolabeled material was applied separately on each marked area of mouse skin and covered with gauze sponge and Bioclusive tape and adhesive tape. Mice were kept in metabolism cages, one animal per cage, and urine samples collected for scintillation counting to determine the quantity of radiolabeled materials being excreted. Parallel studies were conducted simultaneously on non-papain-treated living mice. These studies served as controls against which the treated animals were measured.

1B. In Vivo Studies on Skin Recovery Following Papain Treatment

Experiments were conducted to measure the time required for papain-treated mice to return to normal levels of absorption. These experiments were conducted as described in Example 1A, except that following the removal of papain from the mouse's skin, the mice were maintained separately in metabolism cages for varying periods of time prior to the application of the labeled model compounds. After various time intervals, 150 µl of radiolabeled chemicals were applied separately on the 1 cm$^2$ marked areas on the backs of the mice, where papain had previously been applied. The mice were then kept in separate metabolism cages and at time intervals of 17, 41, and 65 hours, urine was collected and counted using a scintillation counter.

The results of the experiments described in Examples 1A and 1B are presented in the following Table and in FIGS. 1–7.

TABLE 1

Summary of Percent Urinary Recovery of Radiolabeled Chemicals and Protein Immediately and 7 days Following Papain Treatment

| Substance | Time | Percent Recovery |
| --- | --- | --- |
| Citric Acid | Immediate | 4.3% |
| Citric Acid | 7 Days | 0.2% |
| Citric Acid Control (No Papain Treatment) | Immediate | 0.25% |
| Glucose | Immediate | 1.8% |
| Glucose | 7 days | 0.1% |
| Glucose Control (No Papain Treatment) | Immediate | 0.07% |
| Hydrocortisone | Immediate | 24.7% |
| Hydrocortisone | 7 days | 0.6% |

TABLE 1-continued

Summary of Percent Urinary Recovery of Radiolabeled Chemicals and Protein Immediately and 7 days Following Papain Treatment

| Substance | Time | Percent Recovery |
| --- | --- | --- |
| Hydrocortisone Control (No Papain Treatment) | Immediate | 2.5% |
| TEAB | Immediate | 35.4% |
| TEAB | 7 days | 5.3% |
| TEAB Control (No Papain Treatment) | Immediate | 6.2% |
| Albumin | Immediate | 2.7% |
| Albumin | 7 days | 0.0% |
| Albumin Control (No Papain Treatment) | Immediate | 0.0% |
| Lysozyme | Immediate | 16.0% |
| Lysozyme | 7 days | 0.0% |
| Lysozyme Control (No Papain Treatment) | Immediate | 0.0% |
| Insulin | Immediate | 6.0% |
| Insulin | 7 days | 0.0% |
| Insulin Control (No Papain Treatment) | Immediate | 0.0% |

EXAMPLE 2

In Vivo Studies Using Papain-Treated Athymic Nude Mice Skin Immediately and After One or Two Days Recovery Because of some complications encountered during studies utilizing papain treatment by in vivo method (e.g. extended excretion due to storage in various body compartments, delayed response times, etc.) it was decided that additional studies should be conducted wherein the mouse skin was allowed to recover in situ, then excised after various time intervals and evaluated by in vitro permeation methods.

These experiments were conducted by preparing, applying, and occluding papain solutions onto the backs of congenitally athymic nude mice in the same manner as described in Example 1A. At the end of the 24-hour papain treatment, the skin was again cleansed of excess solution. Skin was then excised from part of the animals. The remainder of the animals were housed individually in regular cages for various periods of time (24 hours and 48 hours), after which the treated areas were excised. Immediately following excision of the treated areas, the skins were mounted over Franz-Type, Single-Compartment Diffusion Cells. Four hundred µl of saturated solutions of radiolabeled citric acid, TEAB, glucose, and hydrocortisone were applied, individually, to the exposed surface of the mounted skins on the donor chamber. Saturated solutions of each of these substances were used in order to ensure maximum availability of labeled substances. At varying time intervals, 100 µl samples were removed from the receiver chambers for scintillation counting. All experiments were conducted at 25° C.

FIGS. 8–11 show the saturation concentration of each substance tested, and the flux, permeability coefficient, and graph for each of the substances at the first day (immediately following 24 hours exposure to papain), second day (24 hours following 24-hour exposure to papain), and third day (48 hours following 24-hour exposure to papain).

It can readily be observed that upon only 7 hours exposure, the transdermal penetration of citric acid is about 55 mg from the 1 cm$^2$ section of skin; TEAB is nearly 19 mg, glucose is about 22 mg, and hydrocortisone about 125 μg. Experiments performed after a 48-hour recovery period (3rd day experiments) indicated almost complete skin recovery occurs to pretreatment permeability, as judged by percutaneous data. The low absolute quantity of hydrocortisone (125μg) is probably due to the low solubility of hydrocortisone, even in ethanol, which is the solvent used for hydrocortisone in these examples. All other substances were dissolved in water.

EXAMPLE 3

Hairless mouse skin was pretreated with papain at a concentration of 0.093 mg/ml at pH 7.4 for 24 hours. Afterwards, TEAB was applied. The pretreated skin demonstrated a 33-fold increase in absorption of the TEAB in comparison to normal, untreated mouse skin.

EXAMPLE 4

An enzyme preparation especially useful with ionic drugs (e.g. quaternaries such as acetylcholine chloride; cationics such as alprenolol; and anionics such as warfarin) has the following composition, with a pH adjusted to 7.4:

| Constituent | Concentration |
| --- | --- |
| Papain (sigma) | 0.093 mg/ml |
| Cysteine | 0.10M |
| EDTA | 0.0375M |
| Water | qs |

EXAMPLE 5

The absolute amounts and relative concentrations of an enzyme preparation containing papain to determine skin damage as measured by bleeding of mouse skin was determined.

A. Absolute amount of papain in water and time until bleeding observed

| | |
| --- | --- |
| 0.070 mg/0.250 ml | Observe bleeding at about 0.5 hrs. |
| 0.050 mg/0.180 ml | Observe bleeding at about 1.5 hrs. |
| 0.030 mg/0.108 ml | Observe bleeding at about 5.0 hrs. |
| 0.010 mg/0.108 ml | Do not observe any bleeding for 24 hrs. |

B. Concentration of papain in water and time until bleeding observed

| | |
| --- | --- |
| 0.010 mg/0.108 ml | Do not observe bleeding for 24 hrs. |
| 0.020 mg/0.108 ml | Do not observe bleeding for 24 hrs. |
| 0.030 mg/0.108 ml | Bleeding more or less after 24 hrs. |
| 0.040 mg/0.108 ml | Bleeding more or less after 24 hrs. |

EXAMPLE 6

A. Effect of pH on drug penetration through normal untreated hairless mouse skin Drug penetration through a skin barrier is thought to be a process of passive diffusion and may be described by Fick's First Law:

$$J = -D\frac{dC}{dX}$$

where J is the flux of a drug through a skin barrier, D is the diffusion constant of a drug in the skin barrier, and dC/dX is the concentration gradient of a drug between the vehicle and the skin barrier.

For steady state diffusion:

$$J = \frac{DK}{h} C_v = PC_v$$

where K is the partition coefficient of drug between a skin barrier and the vehicle, $C_v$ is the concentration of drug dissolved in the vehicle, h is the thickness of the skin barrier, and P is the permeability of a drug through the skin barrier.

Enhancement of TEAB penetration through hairless mouse skin by papain:

1. Without papain pretreatment $J = 2.72 \times 10^{-5}$ mg/cm$^2$/sec $P = 2.54 \times 10^{-8}$ cm/sec 2. Pretreated with Sigma papain of concentration 0.010 mg/0.108 ml (0.093 mg/ml)

$J = 6.87 \times 10^{-4}$ mg/cm$^2$/sec $P = 0.85 \times 10^{-6}$ cm/sec $$\text{Ratio of enhancement} = \frac{P \text{ with enhancer}}{P \text{ without enhancer}} = \frac{0.85 \times 10^{-6}}{2.54 \times 10^{-8}} \times 100\% = 3346\%$$

3. Pretreated with Allergan papain of concentration 0.170 mg/0.200 ml (0.850 mg/ml)

$J = 1.04 \times 10^{-3}$ mg/cm$^2$/sec $P = 1.29 \times 10^{-6}$ cm/sec $$\text{Ratio of enhancement} = \frac{1.29 \times 10^{-6}}{2.54 \times 10^{-8}} \times 100\% = 5070\%$$

4. Pretreated with Sigma papain of concentration 0.170 mg/0.602 ml (0.278 mg/ml)

$J = 1.46 \times 10^{-3}$ mg/cm$^2$/sec $P = 1.81 \times 10^{-6}$ cm/sec $$\text{Ratio of enhancement} = \frac{1.81 \times 10^{-6}}{2.54 \times 10^{-8}} = 100\% = 7126\%.$$

| J&P Drug (Class) | pH | | | |
|---|---|---|---|---|
| | 5.9 | 6.6 | 7.4 | 8.0 |
| Acetylcholine Chloride (quaternary) | $J = 5.83 \times 10^{-6}$ mg/cm$^2$/sec | $J = 5.21 \times 10^{-6}$ | $J = 6.41 \times 10^{-6}$ | $J = 9.32 \times 10^{-6}$ |
| | $P = 2.91 \times 10^{-8}$ cm/sec | $P = 2.60 \times 10^{-8}$ | $P = 3.20 \times 10^{-8}$ | $P = 4.66 \times 10^{-8}$ |
| Progesterone (nonionic) | $J = 2.30 \times 10^{-7}$ mg/cm$^2$/sec | $J = 2.34 \times 10^{-7}$ | $J = 2.34 \times 10^{-7}$ | $P = 2.47 \times 10^{-7}$ |
| | $P = 2.88 \times 10^{-6}$ cm/sec | $P = 2.92 \times 10^{-6}$ | $J = 2.92 \times 10^{-6}$ | $J = 3.09 \times 10^{-6}$ |
| Warfarin (anionic) | $J = 1.66 \times 10^{31\ 8}$ mg/cm$^2$/sec | $J = 9.16 \times 10^{-9}$ | $J = 4.68 \times 10^{-9}$ | $J = 4.73 \times 10^{-9}$ |
| | $P = 1.66 \times 10^{-7}$ cm/sec | $P = 9.16 \times 10^{-8}$ | $P = 4.68 \times 10^{-8}$ | $J = 4.73 \times 10^{-8}$ |
| Alprenolol (cationic) | $J = 5.36 \times 10^{-7}$ mg/cm$^2$/sec | $J = 7.74 \times 10^{-7}$ | $J = 1.84 \times 10^{-6}$ | $J = 2.10 \times 10^{-6}$ |
| | $P = 5.36 \times 10^{-8}$ cm/sec | $P = 7.74 \times 10^{-8}$ | $P = 1.84 \times 10^{-7}$ | $P = 2.10 = 10^{-7}$ |

B. Effect of pH on drug penetration through hairless mouse skin pretreated with Sigma papain of concentration 0.093 mg/ml for 24 hours

| J&P Drug | pH | | | |
|---|---|---|---|---|
| | 5.9 | 6.6 | 7.4 | 8.0 |
| Acetylcholine Chloride | $J = 6.00 \times 10^{-4}$ mg/cm$^2$/sec | $J = 7.77 \times 10^{-4}$ | $J = 6.46 \times 10^{-4}$ | $J = 6.28 \times 10^{-4}$ |
| | $P = 3.00 \times 10^{-6}$ cm/sec | $P = 3.88 \times 10^{-6}$ | $P = 3.23 \times 10^{-6}$ | $P = 3.14 \times 10^{-6}$ |
| | $E = 103.09$ | $E = 149.23$ | $E = 100.94$ | $E = 67.38$ |
| Progesterone | $J = 2.88 \times 10^{-7}$ mg/cm$^2$/sec | $J = 3.51 \times 10^{-7}$ | $J = 2.73 \times 10^{-7}$ | $P = 2.89 \times 10^{-7}$ |
| | $P = 3.60 \times 10^{-6}$ cm/sec | $P = 4.39 \times 10^{-6}$ | $P = 3.41 \times 10^{-6}$ | $P = 3.61 \times 10^{-6}$ |
| | $E = 1.25$ | $E = 1.50$ | $E = 1.17$ | $E = 1.17$ |
| Warfarin | $J = 1.27 \times 10^{-7}$ mg/cm$^2$/sec | $J = 1.20 \times 10^{-7}$ | $J = 0.99 \times 10^{-7}$ | $J = 1.21 \times 10^{-7}$ |
| | $P = 1.27 \times 10^{-6}$ cm/sec | $P = 1.20 \times 10^{-6}$ | $P = 0.99 \times 10^{-6}$ | $P = 1.21 \times 10^{-6}$ |
| | $E = 7.65$ | $E = 13.10$ | $E = 21.15$ | $E = 25.58$ |
| Alprenolol | $J = 1.20 \times 10^{-5}$ mg/cm2/sec | $J = 1.33 \times 10^{-5}$ | $J = 1.32 \times 10^{-5}$ | $J = 1.65 \times 10^{-5}$ |
| | $P = 1.20 \times 10^{-6}$ cm/sec | $P = 1.33 \times 10^{-6}$ | $P = 1.32 \times 10^{-6}$ | $P = 1.65 = 10^{-6}$ |
| | $E = 22.39$ | $E = 17.18$ | $E = 7.17$ | $E = 7.86$ |

EXAMPLE 7

Several experiments were performed to determine the enhancement of TEAB penetration through mouse skin with the use of an enzyme preparation containing papain.

Figure 17:
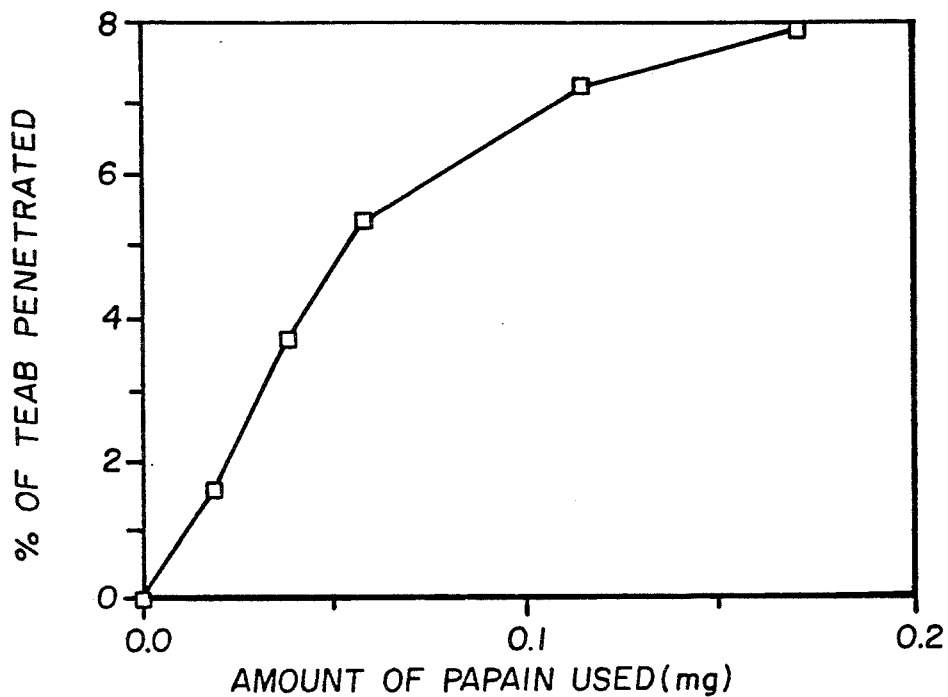
FIG. 17 depicts the enhancement of tetraethylammonium bromide ("TEAB"), a cationic substance, through mouse skin by the use of an enzyme preparation containing papain and an activating agent as per Example 7A.

A. As shown in FIG. 17, the amount of drug penetration through mouse skin in the depicted case TEAB, varies directly with the amount of papain used. In this experiment, varying amounts of Sigma papain, activated with cysteine and EDTA, were used. The percent of TEAB penetration through the skin increased with the amount of activated papain present in the pretreatment enzyme preparation increased.

Figure 18:
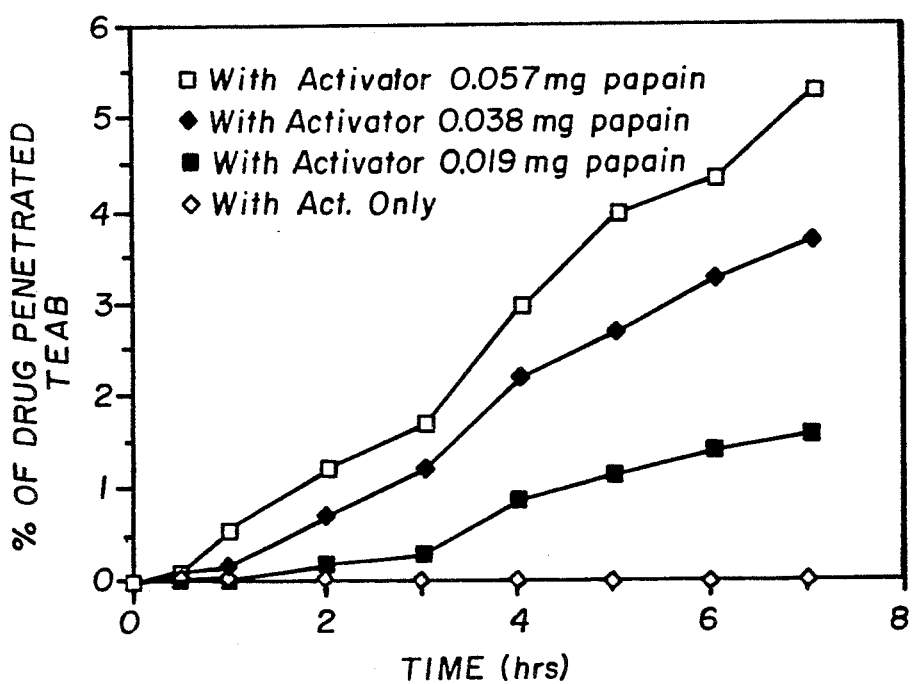
FIG. 18 depicts the enhancement of TEAB penetration through mouse skin by the use of an enzyme preparation containing papain at varying levels and an activating agent as per Example 7B.

B. As shown in FIG. 18, TEAB penetration through mouse skin increases as the amount of papain in the enzyme preparation used to pretreat the skin increases. FIG. 18 also shows that very small amounts of an enzyme in the enzyme preparation are useful in enhancing drug penetration through the skin, and that without the enzyme, drug penetration is not enhanced.

C. As shown in FIG. 19, TEAB penetration is further enhanced by even greater levels of papain in the enzyme preparation pretreatment solution. In the depicted case, Sigma papain of 0.170 mg, 0.113 mg, and 0.057 mg in 0.4–0.6 ml of water were first applied to mouse skin, each with cysteine and EDTA as activating agents.

This example also shows that certain enzyme preparations, such as those containing papain from the Sigma Chemical Company of St. Louis, Missouri preferably include an activating agent such as EDTA and/or cysteine.

EXAMPLE 8

Figure 20:
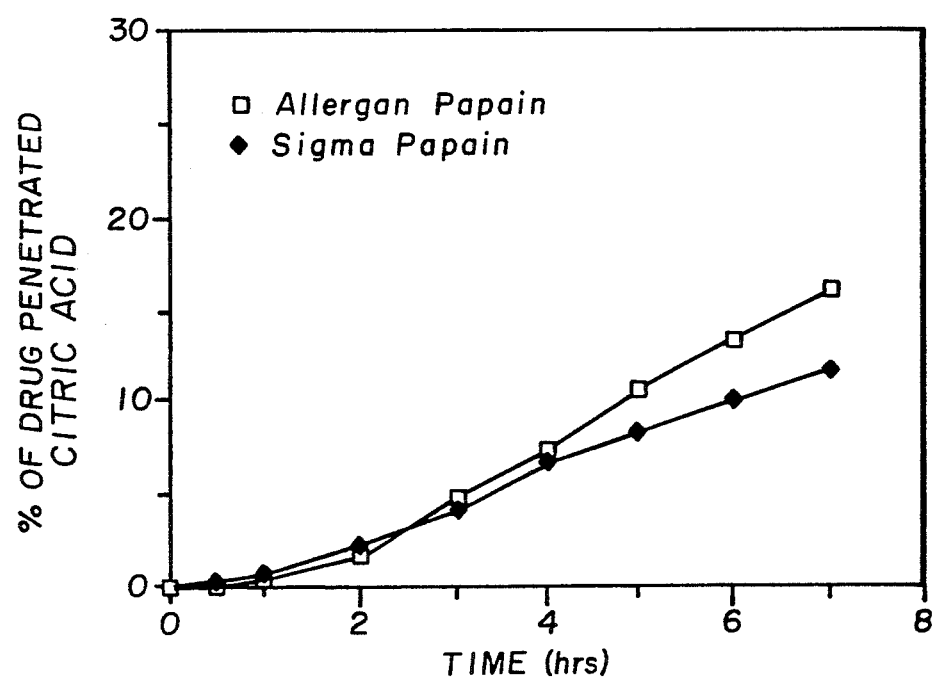
FIG. 20 depicts the percentage of drug (citric acid, an anionic substance) which penetrated through mouse skin at varying times and using various sources of papain in the enzyme preparation as per Example 8.

As shown in FIG. 20, two different sources of papain were used in enhancing the penetration of an anionic chemical, citric acid, through mouse skin. Each enzyme preparation contained 0.170 mg of papain dissolved in 0.1 ml of water. One sample of papain was obtained from Allergan. The other was obtained from Sigma Chemical. Penetration of the anionic chemical was enhanced to a greater extent by the Allergan papain than that of Sigma Chemical. The Sigma Chemical papain was not activated in this experiment.

The preceding examples are exemplary and are not intended to limit the scope of the appended claims which define the invention.

What is claimed is:

1. In a method of applying a percutaneously administrable therapeutic drug for penetration through the skin of an animal, the improvement comprising:

applying an enzyme preparation to a localized area of vital skin of said animal for a predetermined amount of time and in a sufficient quantity to alter the structure of the localized area of vital skin without damaging said skin to facilitate penetration of a drug therethrough;

occluding the localized area of skin with occlusion means during said predetermined amount of time;

removing said occlusion means; and applying an effective amount of said percutaneously administrable therapeutic drug to the localized area of the skin for penetration of said therapeutic drug therethrough.

2. The method according to claim 1 further including the step of occluding the localized area of skin after application of the drug.

3. The method according to claim 1 wherein said predetermined amount of time exceeds 24 hours.

4. The method according to claim 3 wherein said enzyme preparation contains papain and a buffered saline solution.

5. The method according to claim 4 wherein said drug is a cationic chemical.

6. The method according to claim 4 wherein said drug is an anionic chemical.

7. The method according to claim 4 wherein said drug is a highly polar nonionic chemical.

8. The method according to claim 4 wherein said drug is a highly nonpolar, nonionic chemical.

9. The method according to claim 4 wherein said drug is a proteinaceous chemical.

10. The method according to claim 1 further including substantially removing the enzyme preparation from the skin before applying the drug to the localized area of skin.

11. In a method of applying a percutaneously administrable drug for penetration through the skin of an animal, the improvement comprising:

applying an enzyme preparation to a localized area of vital skin of said animal for a predetermined amount of time and in a sufficient quantity to alter the structure of the localized area of vital skin without damaging said skin to facilitate penetration of a drug therethrough;

occluding the localized area of skin with occlusion means during said predetermined amount of time;

removing said occlusion means; and applying an effective amount of said percutaneously administrable drug to the localized area of the skin, said drug being selected from the group consisting of ionic compounds, anionic compounds, cationic chemicals, zwitterionic chemicals, anionic chemicals and nonpolar chemicals.

12. In a method of applying a percutaneously administrable drug for penetration through the skin of an animal, the improvement comprising:

applying an enzyme preparation to a localized area of vital skin of said animal for a predetermined amount of time and in a sufficient quantity to alter the structure of the localized area of vital skin without damaging said skin to facilitate penetration of a drug therethrough;

occluding the localized area of skin with occlusion means during said predetermined amount of time;

removing said occlusion means; and applying an effective amount of said percutaneously administrable drug to the localized area of the skin, said drug being selected from the group consisting of hormones, quaternary compounds, anti-hypertensive agents, anti-nausea agents, anti-arrhythmics, and analgesics.

* * * * *

UNITED STATES PATENT AND TRADEMARK OFFICE
CERTIFICATE OF CORRECTION

PATENT NO. : 5,156,846

DATED : October 20, 1992

INVENTOR(S) : Petersen, et al.

It is certified that error appears in the above-identified patent and that said Letters Patent is hereby corrected as shown below:

In Column 5, line 48, please delete "allergic potential" and insert -- time --;

In Column 5, line 48, please insert -- c) the agent's relative toxicity; d) the agent's allergenic potential; --.

Signed and Sealed this

Nineteenth Day of October, 1993

Attest:

BRUCE LEHMAN

*Attesting Officer*  *Commissioner of Patents and Trademarks*